United States Patent [19]
Hersh et al.

[11] Patent Number: 6,138,683
[45] Date of Patent: *Oct. 31, 2000

[54] SMOKELESS TOBACCO PRODUCTS CONTAINING ANTIOXIDANTS

[75] Inventors: Ted Hersh; Rebecca Hersh, both of Atlanta, Ga.

[73] Assignee: Thione International, Inc., Atlanta, Ga.

[ * ] Notice: This patent is subject to a terminal disclaimer.

[21] Appl. No.: 09/185,172

[22] Filed: Nov. 3, 1998

Related U.S. Application Data

[63] Continuation-in-part of application No. 08/933,696, Sep. 19, 1997, Pat. No. 5,829,449.

[51] Int. Cl.⁷ ............................ A24F 47/00; A24B 15/00
[52] U.S. Cl. .......................... 131/347; 131/352; 424/439; 424/702; 514/959
[58] Field of Search ................................. 131/352–356, 131/298, 334, 347; 424/439, 702, 147.1; 514/959

[56] References Cited

U.S. PATENT DOCUMENTS

| | | |
|---|---|---|
| 4,129,644 | 12/1978 | Kalopissis et al. . |
| 4,144,325 | 3/1979 | Voyt . |
| 4,224,339 | 9/1980 | Van Scott et al. . |
| 4,567,200 | 1/1986 | Tinti et al. . |
| 4,593,043 | 6/1986 | Tinti et al. . |
| 4,602,039 | 7/1986 | Cavazza . |
| 4,617,187 | 10/1986 | Okuyama et al. . |
| 4,710,489 | 12/1987 | Meister . |
| 4,769,382 | 9/1988 | Dubur et al. . |
| 4,818,521 | 4/1989 | Tamabuchi . |
| 4,839,159 | 6/1989 | Winter et al. . |
| 4,865,840 | 9/1989 | Burke et al. . |
| 4,895,727 | 1/1990 | Allen . |
| 4,895,840 | 1/1990 | Burke et al. . |
| 4,927,850 | 5/1990 | Bayless et al. .......................... 514/458 |
| 4,929,442 | 5/1990 | Powell . |
| 4,942,031 | 7/1990 | Levin . |
| 4,961,926 | 10/1990 | Gabrilove . |
| 5,008,119 | 4/1991 | Matsubara . |
| 5,023,235 | 6/1991 | N'Guyen et al. . |
| 5,032,384 | 7/1991 | Yeh et al. . |
| 5,075,102 | 12/1991 | Hubaud et al. . |
| 5,128,365 | 7/1992 | Spector et al. . |
| 5,290,809 | 3/1994 | Ippolito et al. .......................... 514/458 |
| 5,306,486 | 4/1994 | McCook et al. . |
| 5,308,874 | 5/1994 | Sanchez et al. ......................... 514/731 |
| 5,330,757 | 7/1994 | Burke . |
| 5,378,461 | 1/1995 | Neigut . |
| 5,384,116 | 1/1995 | Pawelek et al. . |
| 5,397,770 | 3/1995 | Levin et al. . |
| 5,409,693 | 4/1995 | Perricone . |
| 5,418,253 | 5/1995 | Cavazza et al. . |
| 5,427,778 | 6/1995 | Finkenaur et al. . |
| 5,441,726 | 8/1995 | Mitchnick et al. . |
| 5,486,360 | 1/1996 | Ballagh et al. . |
| 5,494,924 | 2/1996 | Cavazza et al. . |
| 5,516,507 | 5/1996 | N'Guyen et al. . |
| 5,565,439 | 10/1996 | Piazza et al. . |
| 5,582,817 | 12/1996 | Otsu et al. . |
| 5,618,521 | 4/1997 | de Rigal et al. . |
| 5,627,212 | 5/1997 | Cavazza et al. . |
| 5,667,791 | 9/1997 | Hersh et al. . |
| 5,780,489 | 7/1998 | Brooks ..................................... 514/369 |
| 5,829,449 | 11/1998 | Hersh et al. ............................ 131/202 |
| 5,906,811 | 5/1999 | Hersh ........................................ 424/54 |
| 5,922,346 | 7/1999 | Hersh ...................................... 424/439 |
| 6,011,067 | 1/2000 | Hersh ...................................... 514/562 |

FOREIGN PATENT DOCUMENTS

| | | |
|---|---|---|
| 0 516 901 A1 | of 0000 | European Pat. Off. . |
| 3542309 A1 | of 0000 | Germany . |
| WO 80/00427 | of 0000 | WIPO . |
| WO 94/13265 | of 0000 | WIPO . |

*Primary Examiner*—Stanley S. Silverman
*Assistant Examiner*—Jacqueline A. Ruller
*Attorney, Agent, or Firm*—Malcolm B. Wittenberg

[57] ABSTRACT

A composition for inclusion within a quantity of smokeless tobacco. The composition of antioxidants is capable of reducing free radical damage to the oro-pharyngeal cavity of a user resulting from consumption of smokeless tobacco. The composition includes L-glutathione and a source of selenium.

11 Claims, No Drawings

SMOKELESS TOBACCO PRODUCTS CONTAINING ANTIOXIDANTS

RELATED APPLICATIONS

The present application is a continuation-in-part of U.S. application Ser. No. 08/933,696 filed on Sep. 19, 1997, now U.S. Pat. No. 5,829,449.

TECHNICAL FIELD OF THE INVENTION

The present invention deals with the combination of various synergistic antioxidants, enzymatic co-factors, such as selenium-containing compounds and amino acids in appropriate delivery vehicles employed in what is commonly referred to as "smokeless tobacco" as a means of preventing or ameliorating signs and symptoms and complications to the oro-pharyngeal cavity from damage by such products.

BACKGROUND OF THE INVENTION

Tobacco is a substance consisting of the dried leaves and stems of the plant Nicotiana tabacum which contains the addictive drug nicotine. The plant is native to North America but is now grown worldwide. Tobacco abuse has been identified as the single most preventable cause of disease, morbidity and mortality. Tobacco contains and produces many toxic chemicals and free radical species. There are three principal ways to consume tobacco: smoking, chewing and dipping and snuffing. Fifty million Americans smoke, and countless others are affected by tobacco smoke, the so-called secondary or passive smokers. Children of smokers breathe this second-hand smoke and have more respiratory problems than children of non-smokers. Non-smoking spouses and co-workers of smokers have a greater frequency of heart disease than true non-smoker controls.

Smokeless tobacco is used by as many as fourteen million individuals and has a detrimental effect on the oral cavity plus systemic effects from buccal mucosal absorption of nicotine and other injurious chemicals. There is a growing use of smokeless tobacco in adolescents and young adults. Chewing loose leaf tobacco and "dipping" moist, ground snuff tobacco are common uses of tobacco without smoking. "Snuffing" that is "snorting" dry powdered tobacco into the nasal passageways is rarely used in this country. Health risks from smokeless tobacco are still very significant and it is not a substitute for smoking. The alarming growth of use of smokeless tobacco by 10–12 year old users has brought on a massive educational campaign by the National Cancer Institute.

Because of the oro-pharynx's access to the environment, like the skin to oxygen and ultraviolet radiation, the structures of the oral cavity may be damaged by inhaled, ingested or chewed noxious substances and gaseous and particulate materials, as well as injuries by endogenous processes, such as inflammatory reactions and by drugs (xenobiotics). Reactive oxidizing species, as induced by inhaled and chewed tobacco, ozone and nitrous oxide are important factors in generating free radicals and inducing inflammatory reactions.

Leukoplakia, a tobacco induced white patch on the buccal mucosa, as found in smokers, is a localized irritation due to direct contact of smoked or smokeless tobacco and it is directly related to the frequency and years of tobacco abuse. Although leukoplakia is a benign oral lesion, it has a malignant potential, requiring a biopsy of the lesion to rule out cancer. Leukoplakia may regress or resolve completely when use of tobacco products is discontinued. Adequate oral examinations by primary physicians and dentists is paramount to reduce smoke induced mouth and tooth pathology.

Over 30,000 new cases of cancer of the oral cavity are diagnosed annually, accounting for two to four percent of all new cancers. Oral cancer kills 8,000 patients each year and only half of these cases diagnosed annually have a five year survival. The great majority of these patients are users of tobacco products. Other risk factors include alcohol abuse, nutritional deficiencies and poor oral hygiene.

In addition, tobacco contributes to other oral symptoms or pathologies of the mouth, gingiva and teeth. Tobacco may cause halitosis, may numb the taste buds, and interfere with the smell and taste of food. It may stain teeth and contribute to dental caries. Smokers have more dental tartar (calculus) than non-smokers. Tobacco is associated also with gingivitis, with severe periodontal (gum) disease and tooth loss. Acute necrotizing ulcerative gingivitis ("trench mouth") is a destructive, painful inflammatory condition occurring mainly in tobacco abusers.

Besides leukoplakia, another generalized whitish hue on the buccal mucosa represents oral submucous fibrosis. This disease occurs mainly in India and is a chronic, progressive premalignant condition. The etiology is chronic chewing of tobacco or of the areca nut or both. The fibrosis (scarring) results in restriction of mouth opening and involves the palates, tonsillar fossa, buccal mucosa and underlying muscle. Associated with this condition is also oropharyngeal carcinoma, with a high frequency in India and associated in 70% of cases with chewing tobacco. Smokeless tobacco and areca nut usage is also common in Pakistan, Bangladesh and Java and in these individuals and Indian immigrants to the United States and United Kingdom.

The deleterious effects of tobacco abuse are well known and regulatory agencies as well as the public constantly react to these scientific and epidemiologic evidences. Tobacco is indeed a worldwide public health hazard accounting for significant morbidity and mortality.

Cells subjected to oxidative stress resulting from the consumption of smokeless tobacco may severely affect cellular function and cause damage to membrane lipids, to proteins, to cytoskeletal structures and to DNA. Free radical damage to DNA has been measured as formation of single-strand breaks, double-strand breaks and chromosomal aberrations. Cells exposed to ionizing radiation and cigarette smoke have also been demonstrated to have an increased intracellular DNA damage, hence the frequency of oro-pharyngeal, esophageal, and pulmonary carcinomas in tobacco users.

There have been studies of the effects of smokeless tobacco on inflammation and on gingival crevicular levels of prostaglandin E2 and interleukins. Placing a quantity of smokeless tobacco on the buccal mucosa increased the levels of these molecules and there was marked inflammation as a result. It was found that the reaction in the alveolar mucosa was more severe than in the gingiva and ranged from erythema to ulceration supporting the conclusion that smokeless tobacco adversely affects periodontal tissue.

Studies have shown that Maras Powder, a type of smokeless tobacco used in Turkey, affects the micro-nuclei of buccal mucosal cells in habitual users. This provides evidence of the genotoxic effects of smokeless tobacco and its link to oral cancer. Further, it has been shown that smokeless tobacco extracts activate the complement system in in vitro tests using normal human serum. Loose leaf chewing tobacco and dry and moist snuff were studied. The studies showed that these three types of tobacco activated the complement pathway, thus it was postulated that such products provide for putative mechanisms for initiating inflammation in the oral mucosa. The inflammation reaction, in turn, generates countless free radicals which cause further damage to gingival tissues and oral mucosal cell DNA. More recently, it has been demonstrated that nicotine is cytoxic to human primary periodontal ligament and gingiva fibroblast cultures. It was thus concluded that nicotine is a definite risk factor in the progression of periodontal disease. Interestingly, epidemiological studies carried out in Sweden strongly suggest that beer and liquor consumption confer a strong risk factor for oral snuff to induce oral cancers.

The ubiquitous non-enzymatic thiol tripeptide, glutathione (GSH), plays a vital function in maintaining the integrity of the reactive oxygen species-free radical sensitive cellular components. This is accomplished through its direct role as an antioxidant, in its reduced (GSH) form, as well as a cofactor. GSH has been detected in bronchoalveolar lavage fluid. In cells, GSH is oxidized in this process to GSSG, but its cellular concentrations for antioxidant activity is maintained in equilibrium by the enzyme glutathione reductase, consuming NADPH as the source of reducing equivalents. Under states of GSH depletion, including malnutrition and severe oxidative stress, as in smoking and/or chewing tobacco, cells may become injured and die.

SUMMARY OF THE INVENTION

The present invention involves the inclusion of an antioxidant defense system incorporated within smokeless tobacco. The present application utilizes synergistic antioxidants delivered when smokeless tobacco is consumed to prevent and ameliorate free radical damage induced by such products to the oro-pharynx of the user. The invention in its broadest terms comprises glutathione in its reduced form and co-ingredients for regenerating and synergistically working with the reduced form of the glutathione, the latter ingredient comprising selenium preferably as a selenoamino acid such as selenomethione or selenocysteine. As further optional ingredients, it is contemplated that the compositions include ascorbic acid and/or one of its derivatives, a sulphur containing amino acid such as L-cysteine, L-taurine and/or L-methionine, alpha tocopherol and vitamins A. Other antioxidants such as those from green tea and grape seed extracts as known in this industry, may be included as optional ingredients for their antioxidant properties.

DETAILED DESCRIPTION OF THE INVENTION

Without being bound to any particular theory, it is noted that reduced glutathione is employed in protecting cells against oxidative stress by itself being oxidized. Thus, L-glutathione must act in combination with other enzyme systems in order to be reduced so that it may renew its role as a free radical scavenger. GSH functions also coordinately with the enzyme glutathione peroxidase which requires selenium as a cofactor to exert its biologic antioxidant function. Selenium compounds have been shown to scavenge oxygen-centered radicals in vivo with reduced glutathione through glutathione peroxidase. It is believed that selenium-GSH peroxidase catalyzes toxic hydrogen peroxidase in the presence of reduced glutathione. This reaction reduces glutathione to oxidized glutathione GSSG. In turn, the GSSG is reduced back to GSH by the enzyme glutathione reductase thereby maintaining abundant cellular GSH to scavenge free radicals anew.

Further, glutathione and selenium act synergistically in vivo as they are both constituents of the same enzymatic systems. GSH serves as a specific donor substrate while selenium, provided from alimentary sources or locally from intra-oral and topically applied preparations of selenium, or selenoamino acids, provides the prosthetic group of GSH peroxidase. Selenium enhances levels of glutathione peroxidase by enzyme induction. The glutathione and selenium antioxidant functions are intrinsically related since by keeping the peroxidase in action, the GSH and selenium contribute to the removal of the dismutation product of free oxygen radicals, namely, hydrogen peroxide. In a broad sense, GSH and selenium modulate free radical chains initiated or sustained by hydroperoxides. Selenium is used in the present invention for its role as an antioxidant as well as its anticarcinogenic and antimutagenic properties.

It is contemplated that the synergistic antioxidant complex be dispersed in a quantity of smokeless tobacco such as chewing tobacco and snuff. The antioxidant complex can be dispersed as an aqueous emulsion or included in micro encapsulated liposomes to be released as the smokeless tobacco product is consumed. The active ingredients can also be protected by incorporating them in glycospheres and nanospheres. Such vehicles for oral and dermatological uses are well known in the cosmetic and pharmaceutical industries. Liposomes are lecithin spheres that form an oil protective membrane around the active ingredient composition of the present invention. The liposome-entrapped active ingredients travel from the tobacco product and are delivered to the oral cavity where locally they exert both their preventive and therapeutic functions to neutralize the various reactive oxygen and other free radical species. In addition, the antioxidants may also be absorbed as usual by the buccal mucosa for systemic use to counteract further the free radicals generated by the tobacco products.

Loose leaf chewing tobacco is primarily air-cured tobacco, usually treated with licorice and sugars. The antioxidant complex of this invention can be introduced in the processing of tobacco when the flavors are introduced. Instead of digestible sugars, the sweetener is preferably polyol xylitol to help promote oral benefits. Sugars are fermented and thereby cause dental caries and help increase the numbers of micro-organisms in the oral cavity. Xylitol decreases the numbers of streptococcus mutans bacteria in the mouth. Xylitol thereby helps reduce dental cavities and aids in the inflammation in gingivitis and periodontitis caused by the putative bacterial invaders. Plug tobacco is made from heavier grades of leaf from the top of the plant and is free of stems. It is then immersed in mixtures of licorice and sugars and pressed into a plug. It is at this stage of manufacturing that the antioxidant complex of this invention would be introduced. The sugars would be replaced by the polyol sweetener, xylitol. The plug is then covered by a wrapper leaf and re-shaped, so that the plug may be placed by the smokeless tobacco user between cheek and gum. The plug is ordinarily chewed in bites, thus rendering the therapeutic and preventative effects of the antioxidant complex to scavenge and neutralize the free radicals generated by the smokeless tobacco plug.

Twist or roll tobacco is made from cured burley and air-cured and fire-cured leaves. These are flavored and twisted to resemble a rope. The present antioxidants are introduced into the twist or roll after the fire-cured process and the tobacco is cool and ready for flavorings.

Oral snuff, increasing in consumption in the United States, is made from Kentucky and Tennessee fire-cured tobaccos, a process that requires several weeks and multiple stages, plus, unlike the other smokeless types, it undergoes fermentation. Dry snuff is then processed into a powder, wherein the antioxidant complex of this patent application may be introduced, along with flavor and aroma additives, including spices. The U.S. dry snuff which is consumed orally is very similar to the European nasal snuff, to which the antioxidant complex may also be added for its protective benefits.

It is noted that Unger and co-workers have taught therapeutic drug delivery systems comprising gas filled liposomes which encapsulate an active preparation in U.S. Pat. No. 5,580,573 dated Dec. 3, 1996, which is herein incorporated by reference. Earlier, Chakrabarti and associates disclosed preparations comprising a lipid and a modified peptide using liposomes as delivery vehicles. See U.S. Pat. No. 5,380,531 dated Jan. 10, 1995 which is also herein incorporated by reference. Knight and co-workers in U.S. Pat. No. 5,049,388 dated Sep. 17, 1991 which is also herein incorporated by reference, disclosed small particle aqueous aerosol droplets containing liposomes. The patentees taught the inclusion of a drug or medication interacted within the liposome membrane so that when the latter ruptures the active ingredient is not lost from the liposome. The inventors teach various method of preparation of the active particles contained within the liposome. Interacted liposome-drug combination particles are used in small particle treatments.

The active ingredients of the present invention are as follows:
1. L-glutathione in an amount 0.01 to 2.0%, most preferably 0.1 to 1.0%.
2. A source of selenium such as L-selenomethionine or I-selenocysteine at a concentration 0.001 to 1.0%, most preferably 0.01 to 0.10%.

Optional Ingredients
3. L-cysteine and/or its ester, n-acetyl-l-cysteine in a range of 0.01 to 3.0%, most preferably from 0.1 to 1.0%.
4. Vitamin C as ascorbic acid or as an ascorbyl palmitate or other ascorbic acid esters alone or microencapsulated such as in liposomes from 0.05 to 5.0%, preferably 0.1 to 3.0%, most preferably 0.5 to 1.5%.
5. Vitamin E as a powder for dispersion as tocopherol acetate or tocopherol succinate or other esters from 0.05 to 5.0%, preferably 0.1 to 3.0%, most preferably 0.5 to 1.5%. Vitamin E may also be used in liposomes at approximately the same dosages.
6. Vitamin A activity as beta-carotene or a retinyl palmitate or other vitamin A stabilized esters in an amount between 0.05 to 5.0%, preferably 0.1 to 3.0%, most preferably 0.5 to 1.5%. Vitamin A compositions may also be administered by being micro-encapsulated, such as in liposomes.
7. As further optional ingredients the amino acids methionine and/or taurine, as already noted, may be included each in concentrations of at least approximately 0.01 to 3.0%, preferably 0.05 to 2.0%, most preferably from 0.1 to 1.0%.

In the most preferred embodiment of this invention the same ingredients can be introduced in an aqueous solution within the tobacco (chewable or snuff) with the following composition:
1. L-glutathione, at least 0.01 to 2.0%, most preferably 0.1 to 1.0% by weight.
2. L-selenomethione from at least 0.001 to 1.0%, most preferably 0.01 to 0.10%.
3. L-cysteine and/or its ester N-acetyl-L-cysteine from at least 0.01 to 3.0%, most preferably from 0.1 to 1.0%.
4. Ascorbic acid or its esters at 0.05 to 5.0%, preferably 0.1 to 3.0%, most preferably 0.5 to 1.5%.
5. Vitamin E or one of its esters at 0.05 to 5.0%, preferably 0.1 to 3.0%, most preferably 0.5 to 1.5%.
6. Vitamin A or one its esters at 0.05 to 5.0%, preferably 0.1 to 3.0%, most preferably 0.5 to 1.5%.
7. Amino acids, taurine and/or methionine, from 0.01 to 3.0%, preferably 0.05 to 2.0%, most preferably from 0.1 to 1.0%.

In one embodiment of this invention, optional ingredients, particularly exogenous antioxidants may be added to the synergistic complex such as:

| | |
|---|---|
| Japanese green tea (catechins) | approximately 0.5% |
| proauthouganidins | approximately 0.2% |
| Co-enzyme Q | approximately 1.0% |
| N-acetyl-L-carnitine | approximately 0.5% |

In snuff, the active ingredients, that is the antioxidants of the this patent application, may be introduced as a dry powder, either as a mixture of antioxidants, or as a complex in protective liposomes, nanospheres or other acceptable delivery vehicles. This powder may be added in the final process of manufacturing chewing tobacco and snuff and may also contain suitable flavors or fragrances as not infrequently used in this industry.

What is claimed is:
1. A composition for inclusion within a quantity of smokeless tobacco, selected from the group consisting of chewing tobacco and snuff, for reducing free radical induced damage to the oro-pharyngeal cavity of the user, said composition comprising L-glutathione and a source of selenium in combination with said smokeless tobacco.
2. The composition of claim 1 wherein said source of selenium is selected from the group consisting of selenoamino acids, selenomethionine and selenocysteine.
3. The composition of claim 1 further comprising ascorbic acid as a member selected from the group consisting of ascorbyl palmitate and ascorbic acid esters.
4. The composition of claim 1 further comprising a member selected from the group consisting of L-cysteine and N-acetyl-l-cysteine.
5. The composition of claim 1 further comprising vitamin E as a member selected from the group consisting of tocopherol acetate and tocopherol succinate.
6. The composition of claim 1 further comprising vitamin A.
7. The composition of claim 1 further comprising an amino acid selected from the group consisting of methionine and taurine.
8. The composition of claim 1 wherein said smokeless tobacco is chewing tobacco.
9. The composition of claim 1 wherein said smokeless tobacco is snuff.
10. The composition of claim 1 further comprising the inclusion of a sweetener.
11. The composition of claim 10 wherein said sweetener is xylitol.

* * * * *